United States Patent [19]

Wason

[11] 4,312,845

[45] Jan. 26, 1982

[54] METHOD OF PRODUCING AMORPHOUS SILICA OF CONTROLLED OIL ABSORPTION

[75] Inventor: Satish K. Wason, Churchville, Md.

[73] Assignee: J. M. Huber Corporation, Locust, N.J.

[21] Appl. No.: 186,982

[22] Filed: Sep. 15, 1980

Related U.S. Application Data

[63] Continuation-in-part of Ser. No. 74,226, Sep. 10, 1979, abandoned, which is a continuation of Ser. No. 869,347, Jan. 13, 1978, abandoned.

[51] Int. Cl.$^3$ ............................................. C01B 33/187
[52] U.S. Cl. ................................ 423/339; 106/288 B; 252/449; 424/52
[58] Field of Search ............................... 423/338, 339; 106/288 B; 252/449, 451; 424/49, 52

[56] References Cited

U.S. PATENT DOCUMENTS 3,838,192  9/1974  Bertorelli et al. ............... 423/332 Y
3,928,541  12/1975  Wason ................................. 423/339

FOREIGN PATENT DOCUMENTS 2502111  8/1975  Fed. Rep. of Germany ...... 423/339

*Primary Examiner*—Jack Cooper
*Attorney, Agent, or Firm*—Ernest A. Schaal; Harold H. Flanders

[57] ABSTRACT

A new silica is formed by hydrothermally reacting an aqueous dispersion of silica and sodium hydroxide, under certain conditions, to form a partly polymerized silicate; spray drying the mixture to form spheres of polysilicate; reacting the polysilicate with sulfuric acid to form a synthetic amorphous silica; and filtering, washing and drying the synthetic silica. This silica is useful as an adsorbent in polyol purification. When milled and air classified to the proper particle size, it is useful as a polishing agent in dentrifrices and as a flatting pigment in paints.

1 Claim, No Drawings

METHOD OF PRODUCING AMORPHOUS SILICA OF CONTROLLED OIL ABSORPTION

CROSS-REFERENCE TO RELATED APPLICATIONS

This is a continuation-in-part of application Ser. No. 74,226 filed Sept. 10, 1979 entitled SYNTHETIC SILICA AND USES THEREOF which is a continuation of application Ser. No. 869,347 filed Jan. 13, 1978, both now abandoned.

BACKGROUND OF THE INVENTION

This invention relates to a synthetic silica of controlled oil absorption and a method for its preparation. This silica is useful as a polishing agent in dentifrices, as a flatting pigment in paints, and as an absorbent for polyol purification.

SILICAS

Commercially available synthetic silicas are derived either by a liquid process or a vapor process. Products obtained by the vapor process are called fumed or pyrogenic silicas. Products obtained by the liquid process are either silica gels or precipitated silicas (silicon dioxides). Thus, there are three distinct types of synthetic silicas on the market.

1. PYROGENIC SILICAS

Pyrogenic or fumed silicas are prepared by reacting silicon tetrachloride vapor with oxygen and hydrogen gas at high temperatures. These products have high external surface areas.

2. SILICA GELS

Silica gels are of two types—hydrogels and aerogels. Hydrogels are prepared by reacting a soluble silicate, such as sodium silicate, with strong sulfuric acid. The gel is washed salt-free, dried, steam micronized, and then classified. Aerogels are prepared from crude hydrogels by displacing its water content with an alcohol. The alcohol is then recovered by heating the gel in an autoclave.

Aerogels are lighter and fluffier than hydrogels because the shrinkage of the gel structure is avoided during the drying process. Gels have very large surface areas, generally in the range of 300–1,000 sq m/g and high porosities.

3. PRECIPITATED SILICAS

Precipitated silicas are produced by the destabilization and precipitation of the silica from soluble sodium silicates by the addition of a mineral acid such as sulfuric acid or an acidic gas such as carbon dioxide.

When the acid or acidic gas is added to the sodium silicate, the silica starts precipitating. The acid or acidic gas is added until the sodium oxide of the sodium silicate in the silica is less than about one percent by weight. The acid or acidic gas is added to the sodium silicate to neutralize the alkali portion bound to the silicate anion. The reaction slurry is then filtered and washed free of reaction by-product, which is the sodium salt of the acid. The filter cake is dried and milled to obtain a silica of desired degree of fineness.

U.S. Pat Nos. 3,939,262 and 4,007,260, which issued to Keun Y. Kim, discuss silicas prepared by exchanging hydrogen for the sodium ion of a particulate sodium silicate having a silica/sodium oxide ratio of from 1.6 to 3.75, containing only 10 to 25% by weight of water.

In U.S. Pat. No. 3,838,192, a sodium polysilicate is produced by hydrothermal treatment of a dispersion of silica and sodium hydroxide. After the silicate is partly polymerized, the reaction mixture is spray dried, milled and further processed.

SILICAS IN DENTIFRICES

An acceptable dentifrice removes from the teeth stains of various types, food debris, dental plaque, microorganisms and incompletely calcified supragingival calculus. It also dislodges collections of food debris and accumulations of microorganisms from the interproximal spaces between teeth. An abrasive polishing agent is usually included in the dentifrice to accomplish these results. However, the polishing agent must not cause too much abrasion of the enamel surface of the teeth, and it certainly must not scratch or otherwise damage the tooth when used in normal fashion.

The abrasiveness of the dentifrice has most recently been determined by the so-called RDA method of Grabenstetter et al, in their paper "The Measurement of the Abrasion of Human Teeth by Dentifrice Abrasion: A Test Utilizing Radioactive Teeth," J. Dent. Res. 37:1060–1068, 1958. This method utilizes freshly extracted human teeth, which are irradiated, producing the radio nuclide $p^{32}$, a high energy Beta emitter with a half life of 14.3 days. This irradiated tooth is brushed with a mechanical toothbrush, across the dentin. Using a mica end-window Geiger-Muller counter for which the background estimated activity of a dried $p^{32}$ source is $10^{-4}$ microcuries, it is possible to determine $10^{-7}$ g of worn dentin in the abrasive slurry.

Typical polishing agents now used in dental creams are silica xerogels; silica-alumina xerogels; silica-magnesia xerogels; precipitated silicas; sodium alumino silicates and other alkali and alkaline-earth metal alumino silicates.

Amorphous silica is very suitable as a polishing agent in all dentifrices, including visually clear dentifrices. It finds use in clear dentifrices because its refractive index can be easily adjusted to be the same as the refractive indices of humectants used to increase the water affinity of dentifrices. The production of amorphous silica results in a wide distribution of particle size, shape and structure, however, it is sometimes difficult to produce an amorphous silica with the optimum combination of high cleaning ability and low RDA.

U.S. Pat. Nos. 3,939,262 and 4,007,260 discuss a method of reducing the needed humectant concentrations in dentifrice compounds by producing a synthetic amorphous silica having a refractive index lower than that of the humectants. The refractive index of this amorphous silica is in the range of 1.410 to 1.440. U.S. Pat. No. 3,939,262 refers to a translucent dental cream and U.S. Pat. No. 4,007,260 refers to an opaque dentifrice composition. These silicas are prepared by exchanging hydrogen for the sodium ion of a particulate sodium silicate having a silica/sodium oxide ratio of from 1.6 to 3.75, and containing only 10 to 25% by weight of water. The RDA of these dentifrices is 575.

SILICAS AS FLATTING PIGMENTS

A surface that is sufficiently smooth will be glossy. To reduce gloss, one must roughen the surface to break up its smooth outline. In pigmented finishes, this is usually done by increasing the number of pigment particles present in the paint and hence at the surface of the paint. The protruding particles break up the smooth outline. In varnishes or clear wood finishes, reduction in gloss is usually obtained with additives.

Either a few percent of fine particle silica is used, or else an insoluble wax is dispersed in the finish and floats to the surface during drying. The silica, being an extender, is of course transparent when wetted by the finish. Its controlled oil absorption makes a small percentage as effective as a much larger quantity of ordinary pigment.

SILICAS AS POLYOL ADSORBENTS

Potassium is a catalyst used in the manufacture of polyols which are used in the manufacture of polyurethane. When the polyol is manufactured, it will be found to contain residual potassium ions. These potassium ions need to be removed before the polyol is used to make flexible polyurethane. Therefore, the polyol manufacturer needs an adsorbent to remove the residual catalyst if he is to guarantee the quality of his polyol.

The characteristics of an adsorbent of this type should be such that it will filter well, have a reasonable absorption capacity, and not leach any impurities into the polyol. The silica of the present invention has these characteristics.

SUMMARY OF THE INVENTION

An object of this invention is to provide a dentifrice composition with low RDA.

Another object of this invention is to provide a flatting pigment with low gloss.

A further object of this invention is to provide an improved adsorbent for polyol purification.

Other objects and a fuller understanding of the invention may be had by referring to the following description and claims.

The present invention achieves its objectives by forming a synthetic amorphous silica in a four step process.

In the first step, an aqueous dispersion including finely divided silica and a sodium hydroxide is subjected to hydrothermal treatment at a temperature and for a period of time sufficient to react the silica and the sodium hydroxide to form a mixture containing partly polymerized silicate. The temperature of the hydrothermal treatment is in the range of about 138 to 210 degrees Celsius; is preferably from about 154 to 177 degrees Celsius; and is more preferably about 157 degrees Celsius. The length of the hydrothermal treatment is from about 2.5 to 4.5 hours; and is preferably about 3 hours. The dispersion of silica and hydroxide has a silica/sodium oxide weight ratio of at least 1.8:1; preferably from 2.2:1 to 2.6:1; most preferably about 2.4:1.

In the second step, the reaction mixture is spray dried to form minute hollow spheres of sodium polysilicate having a bulk density of from 0.126 to 0.416 g/cc. The temperature at which the polysilicate is spray dried is at least 204 degrees Celsius; is preferably from about 204 to 538 degrees Celsius; and is most preferably at about 316 degrees Celsius.

In the third step, the polysilicate is reacted with a 5 to 15% sulfuric acid solution to form a synthetic amorphous silica, preferably a 11.4% sulfuric acid solution.

In the fourth step, the synthetic silica is filtered, washed and dried.

Optionally, a fifth step can be added wherein the dried silica is milled and air classified to preferred particle size for certain applications as described herein.

The silica is useful as a polishing agent in dentifrice compositions when the above dried silica is milled and air classified so that 100% of the particles are less than about 44 microns. This silica has an oil absorption of greater than about 60 cc/100 g and a BET surface area of between about 40 and 420 sq m/g. A dentifrice containing this silica as a polishing agent has an RDA of less than 500. A typical dentifrice composition would contain from 10 to 50% silica in a solid phase and a liquid phase containing water and a polyhydric alcohol humectant. The humectant is sorbitol, glycerin or mixtures thereof. Fluoride is present in the dentifrice.

This silica is useful as a flatting pigment having a 60 degree gloss of less than 8 when the above dried silica is milled and air classified so that 100% of the particles are less than 10 microns. The silica has an average particle size of from about 2 to 5 microns, an oil absorption of greater than 60 cc/100 g and a BET surface area of between 40 and 420 sq m/g.

This silica is useful as an absorbent for polyol purification, in its unmilled form, having a BET surface area greater than 60 sq m/g, an oil absorption of between 60 and 140 cc/100 g, and at least 70% of the silica is larger than 44 microns. This adsorbent has up to 5% of a metal cation adduct of either aluminum, magnesium, zinc or calcium.

DESCRIPTION OF THE PREFERRED EMBODIMENTS

In its broadest aspect, the present invention is based on the discovery that synthetic silicas can be produced by first hydrothermally reacting an aqueous suspension of finely divided silica and an sodium hydroxide to form a reaction mixture of partly polymerized sodium silicate; then spray during the resulting reaction mixture to form minute hollow spheres of sodium polysilicate having a low bulk density; reacting the spray dried polysilicate with sulfuric acid solution to form a synthetic silica; and then filtering, washing and drying the silica.

In accordance with the present invention, an aqueous dispersion of finely divided silica and sodium hydroxide are subjected to hydrothermal treatment at a temperature and for a period of time sufficient to transform the reactants into sodium silicates that are at least partially polymerized and which contains polysilicate ions in a polymerized, irreversible state.

As used herein, the term finely-divided silica refers to a finely divided powder containing at least 99% silica and having a particle size such that at least 95% of the particles are no larger than 75 microns. Silica powders, referred to in the art as "silica flour" or its equivalent, are suitable.

The hydrothermal treatment of the aqueous dispersion of finely divided silica and sodium hydroxide is effected in a closed vessel at temperatures above the boiling point of the aqueous suspension being treated and under the elevated pressures obtained at such temperatures. Any suitable pressurized equipment may be employed if provided with means for maintaining the aqueous mixture under high agitation and if provided with means (e.g., a steam jacket) for maintaining the dispersion at the desired temperatures and pressures.

In this regard, the hydrothermal treatment of the silica and sodium hydroxide dispersion is conducted at temperatures in the range of from about 138 to 210 degrees Celsius and corresponding pressure of about 5.6 to 21.4 kg/sq cm. A preferred temperature range is from 154 to 177 degrees Celsius and most preferably is 157 degrees Celsius.

The reaction time is a function of the temperature employed. The reaction time must be sufficient to allow the silica and hydroxide to react to form a partly polymerized silicate. Reaction periods on the order of about 2.5 to 4.5 hours are required for the above identified temperature ranges. Higher temperatures result in reduced reaction times, but regardless of the temperature, the reaction time must be sufficient to achieve partial polymerization. A preferred reaction time is about 3 hours.

Sodium silicates having a silica to sodium oxide weight ratio on the order of about 1.5:1 are in simple ionic form. As indicated, the first step is directed to a process for making a sodium polysilicate that is at least partially polymerized. Therefore, the concentration of the reactions must be such that the silica/sodium oxide weight ratio of the product is at least 1.8:1. It has been discovered that products having silica/sodium oxide weight ratios of from about 2.2:1 to 2.6:1, preferably 2.4:1, are particularly advantageous. Thus, the initial composition of the reactants (on a dry basis) is from about 69 to 72 percent by weight silica and from about 31 to 28 percent by weight sodium oxide.

The reaction mixture must be fluid. However, very dilute reaction mixtures case a substantial decrease in the rate of reaction. Preferably, the weight percent of water, based on the total weight of the reaction mixture, is from about 20 to 60%.

In the second step, the reaction mixture is spray dried to form minute hollow spheres of polysilicate having a bulk density of from 0.128 to 0.416 g/cc. The temperature at which the polysilicate is spray dried is at least 204 degrees Celsius, is preferably from 204 to 538 degrees Celsius, and is most preferably at about 316 degrees Celsius.

In the third step, the polysilicate is reacted with a sulfuric acid solution to form a synthetic amorphous silica. The concentration of the sulfuric acid solution may vary from 5 to 15%, but it must be sufficient so that essentially all the sodium ions in the sodium silicate are exchanged for hydrogen ions.

The amount of sulfuric acid solution used must be large enough relative to the amount of sodium silicate to insure that essentially all sodium ions in the solid phase are replaced by hydrogen ions. The use of large amounts of sulfuric acid solution is of no particular advantage and is avoided for reasons of economy. A convenient method for controlling the ratio of acid to silicate is by pH measurement in the reactor. The optimum final pH is from about 2 to about 7.

Adequate reaction time must be provided to allow the exchange of hydrogen ions for sodium ions to go substantially to completion. Completion of the reaction can be recognized by observing the cessation of reaction mixture pH drift. A preferred reaction time is about 1 hour. This reaction may be carried out at any convenient temperature, for example, from about 15 to about 80 degrees Celsius.

In the fourth step the silica is filtered, washed and dried. Because of the granular nature of the starting sodium silicate particles, and because these particles do not appreciably disintegrate during ion exchange, the amorphous silica thus formed can be readily separated from the mother liquor using a filter and washed without difficulty. The silica thus separated does not contain much water and, therefore, requires less drying. The amorphous silica formed is dried in any conventional dryer.

In an optional step, the dried silica is milled and air classified to achieve a particular particle size distribution, the particle size distribution determining the area of usefulness of the silica as described herein.

In the most preferred embodiment, sodium hydroxide in the form of a concentrated solution containing about 50% NaOH is charged to an agitated reaction vessel. Thereafter finely divided silica, which is introduced as an aqueous slurry, is charged to the reaction vessel. The dispersion of silica and sodium hydroxide has an silica/sodium oxide weight ratio of about 2.4:1. The aqueous dispersion is kept under constant agitation during the charging as well as during the reaction period. The concentrated caustic solution is preferably preheated to a reaction temperature of 157 degrees Celsius prior to the introduction of the silica slurry. If the caustic solution is not preheated, the aqueous solution containing the silica and hydroxide is initially heated to the reaction temperature. The aqueous dispersion is subjected to hydrothermal treatment at the reaction temperature for about 3 hours to react the silica and sodium hydroxide to form a reaction mixture of partly polymerized sodium silicate.

At the end of the reaction period, the reaction vessel is vented and the mixture is passed by gravity, into a drop tank which contains dilution water at approximately ambient temperatures. In this manner, the temperature of the reaction mixture is cooled quickly and efficiently and the weight ratio of the reaction product to water is adjusted to the concentration required for the spray drying of the product.

The aqueous mixture in the drop tank is passed through a clarification filter to remove small quantities of insolubles, such as sand, unreacted silica and the like. The clarified aqueous mixture may then be passed into a hold or storage tank or fed directly into the upper portion of a spray dryer.

The aqueous mixture is introduced into the upper portion of the generally upright, cylindrical chamber of the spray dryer and passes through a spray nozzle. The latter causes the aqueous mixture to be finely and evenly dispersed within the chamber and in direct contact with a mass of upwardly directed hot air. Suitable control valves may be provided for regulating the rate of feed of the reaction mixture, as well as that of upwardlly directed air. The spray drying is effected at about 316 degrees Celsius. In a preferred range of spray drying, inlet air temperatures are on the order of from about 204 to 538 degrees Celsius. In this manner, the "flashing off" of the water in the spray dryer is effected rapidly with the resultant spray dried droplets being in the form of hollow microspheres of sodium polysilicate having a bulk density of from 0.128 to 0.416 g/cc.

The sodium polysilicate is then reacted with an 11.4% solution of sulfuric acid solution for sufficient time to replace the sodium ions in the particulate sodium polysilicate with hydrogen ions. The concentration is preferably on the order of 11.4% but other concentrations can be used. The reaction is continued until all of the sodium ions have been replaced. Once the synthetic amorphous silica is produced, it is filtered, washed and dried, and sized as desired for the applications or uses described herein.

The invention will be further illustrated by the following examples which set forth particularly advantageous method and composition embodiments. While the examples are provided to illustrate the present invention, they are not intended to limit it thereto.

PREPARATION OF SODIUM POLYSILICATE

EXAMPLE A

A hollow, spherical sodium polysilicate was prepared by the following process. 4,024 kg of a 50% NaOH solution was charged to a stainless steel autoclave provided with means for continuously agitating the solution. A silica slurry, prepared by dispersing 4,204 kg of silica flour into 2,292 kg of water, was then charged to the reactor. The autoclave was sealed and the temperature of the aqueous mixture was preheated (by the introduction of steam into an exterior steam jacket) to 157 degrees Celsius over a one-hour period producing a pressure of 8.1 kg/sq cm. The reaction mixture was thereafter maintained at this temperature for 3 hours. Continuous agitation was maintained throughout the heat-up and reaction period. At the end of the three-hour reaction cycle, the steam was shut off and the autoclave partially vented to reduce the pressure to about 5.3 kg/sq cm. The vent was then fully opened and the reaction mixture fed by gravity into a drop tank positioned beneath the autoclave and containing 6,869 kg of water at 25 degrees Celsius. The mixture in the drop tank was pumped through a classification filter and introduced into the upper portion of a spray dryer.

The aqueous mixture was fed into the spray dryer at a rate of 9,571 kg per hour, the concentration of the mixture comprising 0.48 kg of sodium polysilicate per liter. The speed of the spray nozzle was about 11,000 rpm. The spray dryer inlet and outlet air temperatures were 316 and 93 degrees Celsius, respectively. The spray dried product was collected and withdrawn from the base of the spray dryer by a screw conveyor. 5,661 kg of sodium polysilicate, having a silica/sodium oxide weight ratio of 2.4:1 and a density of 0.128 g/cc was recovered from the spray dryer. The fact that the product produced in this example was partially polymerized was established by conductivity tests as determined by the Harman technique, set forth in R. W. Harman, *Journal of Physical Chemistry* 32, 44–60 (1928).

EXAMPLE B

The procedure of Example A was repeated except that the temperatures and pressures of the hydrothermal reaction were varied in a series of examples as shown by the following table.

TABLE I

| Run No. | Temperature (Celsius) | Pressure kg/sq cm | Reaction time (min.) |
|---|---|---|---|
| 1 | 127 | 4.5 | 270 |
| 2 | 138 | 5.5 | 240 |
| 3 | 160 | 8.3 | 180 |
| 4 | 177 | 11.5 | 175 |
| 5 | 193 | 15.8 | 160 |
| 6 | 210 | 21.4 | 150 |

The products obtained in these runs were the same as that obtained in Example A. From the Table, it may be seen that an increase in the temperature and pressure increases the rate of the hydrothermal synthesis.

Further, it was noted that hydrothermal reactions conducted at temperatures below 127 degrees Celsius produced little polysilicate transformation even for reaction periods on the order of 10 hours or longer.

EXAMPLE C

In a series of tests, the procedures of Example A were repeated except that the quantities of reactants in the hydrothermal treatment were varied as indicated.

TABLE II

| Run No. | Reactants, wt. percent | | | Product silica/sodium oxide wt. ratio obtained |
|---|---|---|---|---|
| | silica | Na OH | water | |
| 1 | 39.0 | 21.6 | 39.4 | 2.3 |
| 2 | 42.5 | 17.7 | 39.8 | 2.5 |
| 3 | 43.4 | 16.6 | 40.0 | 2.6 |
| 4 | 43.8 | 16.2 | 40.0 | 2.7 |

PREPARATION OF SILICAS

Example I 848 g of the sodium polysilicate of Example A was added to 3000 ml of 11.4% sulfuric acid in 55 minutes. The reaction slurry (pH of 2.0) was filtered in a Buchner filter. The wet cake was washed with tap water and dried at 150 degrees Celsius. Pertinent data is set forth in Table III.

Example II

The procedure of Example I were repeated except that: (1) the density of the sodium polysilicate was 0.348 g/cc; (2) 1077 g of sodium polysilicate was added to the acid solution in 50 minutes; and (3) the final pH of the reaction slurry was 4.7. Pertinent data is set forth in Table III.

Example III

The procedures of Example I were repeated except that 485 g of sodium polysilicate was added to 3000 ml of 5.7% sulfuric acid in 50 minutes, and the final pH was 5.3. Results of the experiment are listed in Table III.

Example IV

The procedures of Example I were repeated except that: (1) the density of the sodium polysilicate was 0.416 g/cc; (2) 1045 g of sodium polysilicate was added to the acid solution in 40 minutes; and (3) the final pH of the reaction slurry was 4.0. Results of the experiment are listed in Table III.

Example V

The procedures of Example I were repeated except that: (1) the density of the sodium polysilicate was about 0.416 g/cc; (2) 525 g of sodium polysilicate was added to 3000 ml of 5.7% sulfuric acid in 50 minutes; and (3) the final pH of the reaction slurry was 6.0. Results of the experiment are listed in Table III.

TABLE III

| UNMILLED SILICA | | | | | |
|---|---|---|---|---|---|
| | EXAMPLE | | | | |
| | I | II | III | IV | V |
| Sulfuric Acid, % | 11.4 | 11.4 | 5.7 | 11.4 | 5.7 |
| Density, g/cc | 0.128 | 0.348 | 0.128 | 0.416 | 0.416 |
| Final pH, reaction | 2.0 | 4.7 | 5.3 | 4.0 | 6.0 |
| Reaction time, min. | 55.0 | 50.0 | 50.0 | 40.0 | 50.0 |
| % Wet Cake Moisture | 74.0 | 73.5 | 82.5 | 70.5 | 80.0 |
| BET Surface Area, sq m/g | 25.0 | 92.0 | 55.0 | 436.0 | 281.0 |
| Oil Absorption, | | | | | |

TABLE III-continued

| UNMILLED SILICA | | | | | |
|---|---|---|---|---|---|
| | EXAMPLE | | | | |
| | I | II | III | IV | V |
| cc/100g | 59.0 | 42.0 | 120.0 | 68.0 | 73.0 |

From these examples, it may be seen that the surface area and oil absorption can be controlled by varying the sodium polysilicate density in the reaction.

Examples VI–X

In Examples VI through X, the silica of Examples I through V respectively, was milled and air classified. The resulting product properties are listed in Table IV showing changes in the BET surface area and oil absorption.

TABLE IV

| MILLED SILICA | | | | | |
|---|---|---|---|---|---|
| | EXAMPLE | | | | |
| | VI | VII | VIII | IX | X |
| BET Surface Area, sq m/g | 45.0 | 111.5 | 76.0 | 405.0 | 324.0 |
| Oil Absorption, cc/100g | 73.0 | 65.0 | 156.0 | 79.0 | 78.0 |

DENTIFRICE COMPOSITION

When the synthetic silica of the present invention is milled and air classified so that 100% of the particles are less than 44 microns, the silica is useful as a polishing agent in dentifrice compositions. This silica has an oil absorption of greater than 60 cc/100 g and a BET surface area of between 40 and 420 sq m/g. Such a dentifrice composition is loaded with silica in the solid phase of loading levels of 10 to 50% by weight. The liquid phase of the compound comprises basically water and a polyhydric alcohol humectant to increase the water affinity of the dentifrice. The polyhydric humectant is either glycerine, sorbitol or a mixture thereof.

Other ingredients in the liquid phase can be small amounts of flavorings, sweetening agents and sudsing agents.

Examples of suitable flavorings are oil of wintergreen, oil of peppermint, oil of spearmint, oil of sassafras and oil of anise.

Examples of sweetening agents are saccharin, dextrose, levulose and sodium cyclamate.

Examples of suitable sudsing agents are water-soluble alkyl and alkyl ether sulfates and sulfonates having alkyl groups of from 8 to 18 carbon atoms; water soluble salts of sulfonates; monoglycerides of fatty acids having from 10 to 18 carbon atoms; water-insoluble salts of sulfated fatty alcohols having from 10 to 18 carbon atoms; salts of fatty acid amides of taurines; salts of fatty acid esters of isethionic acid; and salts of substantially saturated aliphatic acyl amides of saturated aliphatic monoaminocarboxylic acids having from 2 to 6 carbon atoms in which the acyl radical contains from 12 to 16 carbon atoms, such as sodium N-lauryl sarcoside. These sudsing agents are generally used in an amount of from 0.5 to 5.0% by weight, based on the weight of the dentifrice composition.

Fluoride ions are present in the liquid phase. The fluoride ions can be supplied by an innocuous water-soluble fluoride compound which is capable of providing at least 100 ppm of fluoride ions on contact with water. The term fluoride ion includes $F^-$ and complex fluoride ions such as $PO_3F^-$. The term "innocuous" means a compound which is not undesirably toxic, highly colored, or otherwise objectionable for use in a dentifrice. Suitable innocuous fluoride compounds include many water-soluble inorganic fluoride salts and many complex water-soluble fluoride containing salts.

In addition to the aforementioned ingredients, it may also be necessary to add various thickening materials in order to obtain the proper consistency in certain toothpastes. Examples of such thickening materials are water-soluble salts of cellulose ethers such as sodium carboxymethylcellulose and sodium carboxymethyl hydroxyethyl cellulose. Natural gums such as gum karaya, gum arabic, and gum tragacanth also can be used as thickeners but may tend to cause undesirable odors or flavors in some formulations. Coloring agents, preservatives, as well as irridescent or pearlescent flakes may also be used.

All of the aforementioned ingredients may be incorporated in any order to formulate dentifrice compositions.

The dentifrice will be further illustrated by the following examples which set forth particularly advantageous method and composition embodiments. While the examples prove to illustrate the present invention they are not intended to limit it thereto.

Examples XI through XIII show how a dentifrice of the present invention compares to the dentifrice of Example II of U.S. Pat. No. 3,939,262 (the only example where a spray dried silicate was used to form silica in that patent).

CONTROL (Process of U.S. Pat. No. 3,939,262)

50 grams of spray-dried HSS (Philadelphia Quartz GD Grade) containing 55% silica, 27.5% sodium oxide, 17.5% water, having a bulk density of 0.97 g/cc, and having a silica/sodium oxide ratio of 2, were slowly added with agitation to a vessel containing 2.5 liters of 1.0% aqueous solution of sulfuric acid and reacted over a three hour period at room temperature. During this reaction the pH was 6.8. The solid was very easily filtered through a Buchner filter and digested in 1 liter of water for 1 hour. The solid was filtered and dried in a drying oven at 160 degrees Celsius for 36 hours.

The resulting silica had an average refractive index between 1.412 and 1.416 and contained: silica, 92.0%, soluble sodium oxide, 0.35%; $SO_4$, lesser than 0.1%; and water 800 degrees Celsius ignition, 6.48%.

A dental cream was prepared containing:

| | | |
|---|---|---|
| Sorbitol - 57% | 64.73% | |
| Glycerol | 5.00% | |
| CMC (Carboxymethyl-cellulose) | 1.30% | anhydrous basis |
| Saccharin | 0.20% | |
| METHYL PARASEPT (methyl ester of para-hydroxy-benzoic acid) | 0.04% | |
| PROPYL PARASEPT (propyl ester of para-hydroxy-benzoic acid) | 0.01% | |
| Amorphous Silica of this Example | 26.00% | anhydrous basis |
| Flavor | 1.15% | |
| | 100.00% | |

The oil absorption of the silica was 33 cc/100 g and the RDA of the dentifrice was 575 as reported in U.S. Pat. No. 3,939,262.

Example XI

The silica of Example IX was milled and air classified so that 100% of the particles were smaller than 44 microns, after which it was incorporated in a dental cream of the following formulation.

| | | |
|---|---|---|
| Sorbitol | 64.73% | |
| Glycerol | 5.00% | |
| CMC | 1.40% | anhydrous basis |
| Saccharin | 0.20% | |
| METHYL PARASEPT | 0.04% | |
| PROPYL PARASEPT | 0.01% | |
| Amorphous silica of this Example | 26.00% | anhydrous basis |
| Sodium lauryl sulfate | 1.47% | |
| Flavor | 1.15% | |
| | 100.00% | |

This dentifrice had an RDA of 415.

Example XII

The silica of Example VI was milled and air classified so that 100% of the particles were smaller than 44 microns, then it was evaluated for RDA without incorporating it in the dentifrice matrix. The resulting RDA was 441.

Example XIII

Example XI was repeated except that the silica of Example VII was used instead of the silica of Example IX. The resulting RDA was 80.

Thus, in operation, a dentifrice composition with an RDA of less than 500 is formed by using as a polishing agent, a synthetic silica with an oil absorption greater than 60 cc/100 g and a BET surface area between 40 and 420 sq m/g produced by hydrothermally reacting, under certain controlled conditions, an aqueous suspension of finely divided silica and an alkali metal hydroxide to form a partly polymerized silicate; spray drying the resulting reaction mixture to form spheres of alkali metal polysilicate; reacting the dried polysilicate with sulfuric acid to form a synthetic silica; filtering, washing and drying the silica; then milling and air classifying the silica so that 100% of the particles are less than 44 microns.

FLATTING PIGMENT

When the synthetic silica of the present invention is milled and air classified so that 100% of the particles are less than 10 microns, the average particle size is between 2 and 5 microns and the silica makes a good flatting pigment with a 60 degree gloss of less than 8. The invention will be further illustrated by the following example. While the example proves to illustrate the present invention, it is not intended to limit it thereto.

Example XIV

The silica of Example VI was milled and air classified so that 100% of the particles were smaller than 10 microns, with an average particle size of 5 microns. This silica was mixed with 350 grams of the nitro-cellulose lacquer (conforming to Military Specification MIL-L-10287A-amendment 2, Type II, of Aug. 27, 1959 issue) and mixed for 3 minutes using the low speed setting of the Hamilton-Beach No. 30 mixmaster. The lacquer containing dispersed silica was tested for Hegman fineness of grind (5.50) and cleanliness of grind.

The lacquer containing dispersed silica was mixed with additional lacquer (if needed) to prepare stock solutions containing 10%, 3.5%, and 1.75% by weight of vehicle solids. A drawdown of various stock solutions (containing 10%, 3.5% and 1.75% silica in lacquer) was made on carrara glass using a No. 34 wire wound coating application rod. Carrara glass drawdowns were allowed to dry for 45 minutes under dust-free conditions. Using the above method, drawdowns were also made from stock solutions containing the silica developed via the prior art processes.

Using the Gardner multi-angle gloss meter, the gloss and sheen values of the various drawdowns were measured at 60 and 85 degrees, respectively. The Hegman grind of the new silica was 6.0, and 60 degree gloss was 7, and 85 degree sheen was 12 when the lacquer contained 10% by weight of synthetic silica.

Example XV

The silica of Example VIII was milled and air classified so that 100% of the particles were smaller than 10 microns. The average particle size was 2 microns.

Thus, in operation, a flatting pigment with a 60 degree gloss of less than 8 is formed using a synthetic silica having an oil absorption greater than 60 cc/100 g and a BET surface area of between 40 and 420 sq m/g produced by hydrothermally reacting, under certain controlled conditions, an aqueous suspension of finely divided silica and an alkali metal hydroxide to form a partly polymerized silicate; spray drying the resulting reaction mixture to form spheres of alkali metal polysilicate; reacting the polysilicate with sulfuric acid to form a synthetic silica, filtering, washing and drying the silica, then milling and air classifying the silica so that 100% of the particles are less than 10 microns with an average particle size of from 2 to 5 microns.

ABSORBENT FOR POLYOL PURIFICATION

Silicas with a BET surface area greater than 60 sq m/g; an oil absorption of between 60 and 140 cc/100 g; and at least 70% of the silica particles larger than 44 microns are particularly useful as adsorbents for polyol purification.

The characteristics of a good adsorbent for polyol purification are: (1) it should filter well, (2) it should have a reasonable adsorption capacity, and (3) it should not leach any impurities into the polyol.

Silicas which have at least 70% of the particles larger than 44 microns are so coarse as to filter exceptionally well.

Silicas having an oil absorption of between 60 and 140 cc/100 g, have reasonable adsorption capacity.

Silicas, being basically pure silica, have no impurities to leach into the polyol.

Thus, the silicas described above are good adsorbents for polyol purification.

These silicas can be made as described by hydrothermally reacting, under certain controlled conditions, an aqueous suspension of finely divided silica and an alkali metal hydroxide to form a partly polymerized silicate; spray drying the resulting reaction mixture to form spheres of sodium polysilicate; reacting the polysilicate with an acidic solution to form a synthetic silica; and then filtering, washing and drying the silica. This process is described in detail in the first part of the description of the preferred embodiments.

When up to 5% of a metal cation adduct, such as aluminum, magnesium, zinc, or calcium is added to any of the adsorbents above, there is a significant improvement in surface area.

Example XVIII

The adsorption capacity of silica adsorbent for the alkaline component (residual catalyst) in polyol was determined by first preparing a polyol solution containing 0.3% potassium hydroxide (KOH). The adsorbent was mixed with the polyol—KOH solution and after a specified length of time the polyol was filtered. The residual concentration of KOH in the filtrate was determined by atomic absorption (AA) spectroscopy.

In the actual test method a 3-neck flask was used and fitted with an agitator and thermometer. 200 grams of crude polyol containing 0.3% KOH was added to the 3-neck flask. The polyol solution was heated to 95 degrees Celsius and then 2 grams of synthetic silica absorbent was added. The absorbent polyol mixture was heated for 40 minutes and then filtered immediately into a 7 centimeter diameter Buchner funnel using a No. 1 Whatman filter paper. The filtrate was analyzed for residual KOH. The following data were obtained (see Table V).

TABLE V

| Silica Adsorbent | % Residual KOH in Filtrate | Silica Adsorption Capacity mg KOH/g |
|---|---|---|
| From Example IV | 0.10 | 200 |
| From Example V | 0.08 | 220 |

From data in Table V, it is clear that synthetic silicas of the present invention can be efficiently used to remove traces of alkaline catalyst impurities such as KOH from polyols.

While the present invention has been described with reference to specific embodiments, this application is intended to cover those various changes and substitutions which may be made by those skilled in the art without departing from the spirit and scope of the appended claims.

I claim:

1. A method of producing a synthetic amorphous silica useful as a polishing agent in a dentifrice comprising a solid phase comprising from 10 to 50% by weight of the dentifrice, of said synthetic amorphous silica and a liquid phase comprising water and a polyhydric alcohol humectant selected from the group consisting of sorbitol, glycerin and mixtures thereof; wherein fluoride is present in the dentifrice composition and the dentifrice has an RDA of less than 500 when the silica has 100% of the particles below 44 microns, an oil absorption greater than 60 cc/100 g and a BET surface area between 40 and 420 sq. m/g; as a flatting pigment in a paint coating composition wherein said flatting pigment has a 60 degree gloss of less than 8 when the silica has 100% of the particles below 10 microns and having an average particle size of from 2 to 5 microns, an oil absorption greater than 60 cc/100 g and a BET surface area between 40 and 420 sq. m/g; and as an adsorbent for polyol purification when the silica has at least 70% of the silica larger than 44 microns, an oil absorption of from 60 to 140 cc/100 g and a BET surface area greater than 60 sq. m/g when the synthetic silica contains up to 5% by weight of a metal cation adduct selected from the group consisting of aluminum, magnesium, zinc and calcium, said method comprising the steps of:

(a) subjecting an aqueous dispersion including finely divided silica and a sodium hydroxide to hydrothermal treatment at a temperature in the range of from about 138 to 210 degrees Celsius and for a period of time of from about 2.5 to 4.5 hours and sufficient to react the silica and said sodium hydroxide to form a reaction mixture of partly polymerized sodium silicate, said aqueous dispersion having a silica to sodium oxide weight ratio of at least 1.8:1;

(b) spray-drying said reaction mixture at a temperature of at least 204 degrees Celsius to form minute hollow spheres of sodium polysilicate having a bulk density of from 0.128 to 0.416 g/cc;

(c) reacting the polysilicate with a 5 to 15% sulfuric acid solution to form a synthetic amorphous silica; and (d) filtering, washing and drying the synthetic amorphous silica.

* * * * *

UNITED STATES PATENT AND TRADEMARK OFFICE
CERTIFICATE OF CORRECTION

PATENT NO. : 4,312,845
DATED : January 26, 1982
INVENTOR(S) : SATISH K. WASON

It is certified that error appears in the above—identified patent and that said Letters Patent is hereby corrected as shown below:

ON THE TITLE PAGE:
In Abstract, next to last line, "dentrifrices" should be -- dentifrices --.

Column 1, line 17, "absorbent" should be -- adsorbent --.

Column 4, line 23, "absorbent" should be -- adsorbent --.

Column 4, line 36, "an sodium" should be -- a sodium --.

Column 4, line 38, "during" should be -- drying --.

Column 5, line 29, "case" should be -- cause --.

Column 6, line 50, "upwardlly" should be -- upwardly --.

Column 12, line 36, "ABSORBENT" should be -- ADSORBENT --.

Column 13, line 18, "absorbent" should be -- adsorbent --.

Signed and Sealed this

Thirteenth Day of April 1982

[SEAL]

Attest:

GERALD J. MOSSINGHOFF

*Attesting Officer*   *Commissioner of Patents and Trademarks*